United States Patent [19]

Gouda

[11] 4,350,159
[45] Sep. 21, 1982

[54] FRAME FOR STEREOTACTIC SURGERY

[76] Inventor: Kasim I. Gouda, 34 Sierra Rd., Readville, Mass. 02136

[21] Appl. No.: 125,868

[22] Filed: Feb. 29, 1980

[51] Int. Cl.³ .............................................. A61B 19/00
[52] U.S. Cl. ................................................. 128/303 B
[58] Field of Search ............... 128/303 B, 303.19, 791, 128/784, 644, 642; 33/174 D; 250/491

[56] References Cited

U.S. PATENT DOCUMENTS 3,061,936 11/1962 Dobbeleer ...................... 33/174 D
3,357,431 12/1967 Newell ............................. 128/303 B
3,508,552 4/1970 Hainault ......................... 128/303 B

FOREIGN PATENT DOCUMENTS 2139433 2/1973 Fed. Rep. of Germany ... 128/303 B

OTHER PUBLICATIONS

Willis, Jr.–Medical Neurobiology, Mosby Co., St. Louis; 1973 pp. 150–152.

Primary Examiner—Michael H. Thaler
Attorney, Agent, or Firm—Milton Oliver; David Wolf

[57] ABSTRACT

A stereotactic instrument for precise insertion of an electrode in the brain for treatment of certain nervous system disorders, such as Parkinson's disease. A rectangular frame surrounds the head and is supported by four pins pressed against the skull. The front and back segments of the frame support radio-opaque vertical markers for alignment with the midline of the brain. The left and right segments each support a pair of adjustable radio-opaque markers for alignment with the anterior and posterior commissures of the brain. Adjustment is by turning knobs connected to a rod and gear system. Bridges between anterior and posterior markers parallel a reference line between the commissures of the brain's third ventricle. Adjustable brackets on the bridge support an arc bearing an electrode carrier.

3 Claims, 5 Drawing Figures

FRAME FOR STEREOTACTIC SURGERY

BACKGROUND OF THE INVENTION

[1] Field of the Invention

The present invention relates to stereotactic instruments used by surgeons to precisely introduce electrodes deep into the brain and more particularly to a stereotactic instrument which obviates the need to take many X-ray photos and correct them for beam spreading and rotation of the head in relation to the axis of the X-ray beam.

[2] Description of the Prior Art

Horsley and Clarke used stereotactic instruments on experimental animals as long ago as 1908 (*Brain* 31:45-124). Kirschner introduced use of stereotactic instruments for electrocoagulation in humans in 1933 (*Arch. Klin. Chir.* 176:581-620) and Spiegel and Wycis described their use in intracerebral surgery in 1947 (*Science* 106:349-350). Numerous other models have been described in neurological journals. Most, however, require radiological correction in use, cf. Mark, McPherson and Sweet, *Am. J. Roentgenology* 71:435-444 (1954).

Correction frequently requires calculation of how far an X-ray has diverged from the central axis of the beam by the time it passes through a particular part of the brain and strikes the film or detector. Such calculations, particularly if they must be done for each of a series of X-rays, undesirably prolong the surgical procedure and the length of time the patient spends under anesthesia. Frequently, X-rays must be repeated for each additional target.

SUMMARY OF THE INVENTION

Accordingly, a primary object of the present invention is to eliminate the need for radiological correction in using the stereotactic instrument.

A further object is to permit any radial approach to the target once the instrument has been adjusted to the coordinates of the target.

Still another object is to facilitate the reaching of a symmetrically disposed second target in the opposite hemisphere of the brain without re-adjustment of the instrument or additional X-rays.

Yet another object is to speed up the surgical procedure and allow it to be done under local anesthesia.

FEATURES OF THE INVENTION

To accomplish these and other objects, the stereotactic device of this invention has among its many features a rectangular frame for mounting around a patient's head by means of pins tapped into the skull. Frame segments to the left and right of the head each act as runners for a pair of adjustable blocks bearing radioopaque anterior (front) and posterior (back) reference markers. Gearboxes at each corner of the frame connected by rods interpenetrating the four blocks allow separate vertical and anterior-posterior adjustment of the anterior and posterior marker pairs by means of four adjusting knobs on the left side of the frame. A bridge fits atop the left blocks, replacing the left anterior and left posterior markers, and another fits atop the right blocks. A set of interlocking calibrated adjustable brackets fits atop each bridge and supports one of the ends of an arc pivotable around the head. The arc slidably supports an electrode carrier for placement of an electrode in the brain at any desired radial angle. The center of curvature of the arc defines the target and can be displaced in the vertical, horizontal and lateral dimensions through ranges of about 55 mm. each by adjusting the brackets supporting the arc.

BRIEF FIGURE DESCRIPTION

These and other objects, features and advantages of the invention will appear from the following description of a preferred embodiment, as shown in the attached drawings, in which.

DETAILED DESCRIPTION OF THE DRAWINGS

Figure 1:
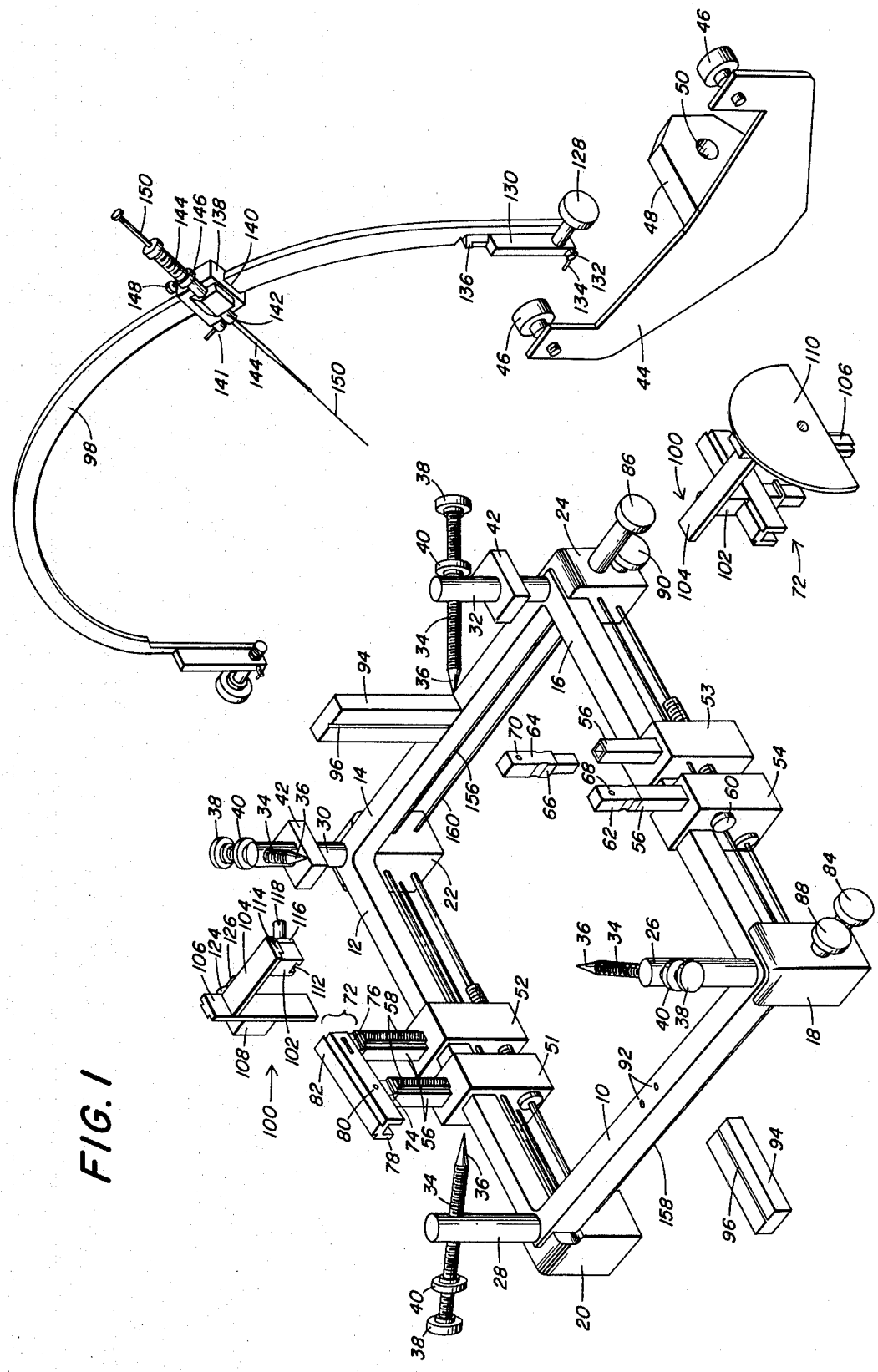
FIG. 1 is a perspective view of the stereotactic device and all components used in different phases of the use of the invention, taken from the left front corner.

There is shown in FIG. 1 a preferred embodiment of the stereotactic device having a rectangular frame comprising a front segment 10, a right segment 12, a rear segment 14 and a left segment 16. Some of the components illustrated in this figure, as hereinafter described, are not used simultaneously but rather are used on the frame in sequence. However, to illustrate their relative locations, they are all illustrated in this figure together. Depending from the left front, right front, right rear and left rear corners of the frame are gearboxes 18, 20, 22 and 24, respectively. Atop the same corners of the frame are internally threaded posts 26, 28, 30 and 32, respectively.

Each post receives a long horizontal skull support screw 34 tipped by a sterile point 36 for insertion into the skull. In the preferred embodiment, the screws project inward from the corners of the frame at a fixed angle to the frame segments 10, 12, 14 and 16. The outward ends of the screws 34 bear knurled knobs 38 and counter nuts 40 are threaded on screws 34 between the posts and knobs 38.

Mounted around rear posts 30 and 32 between frame segment 14 and the holes for screws 34 are rectangular collars 42 for attachment of the frame to a conventional Mayfield headrest by means of U-shaped bracket 44. The tips of bracket 44 are pierced by a pair of screws 46 which fit into threaded holes in the rear faces of collars 42. A vertical flange 48 pierced by a horizontal hole 50 projects from the surface of bracket 44 away from the frame.

Figure 2:
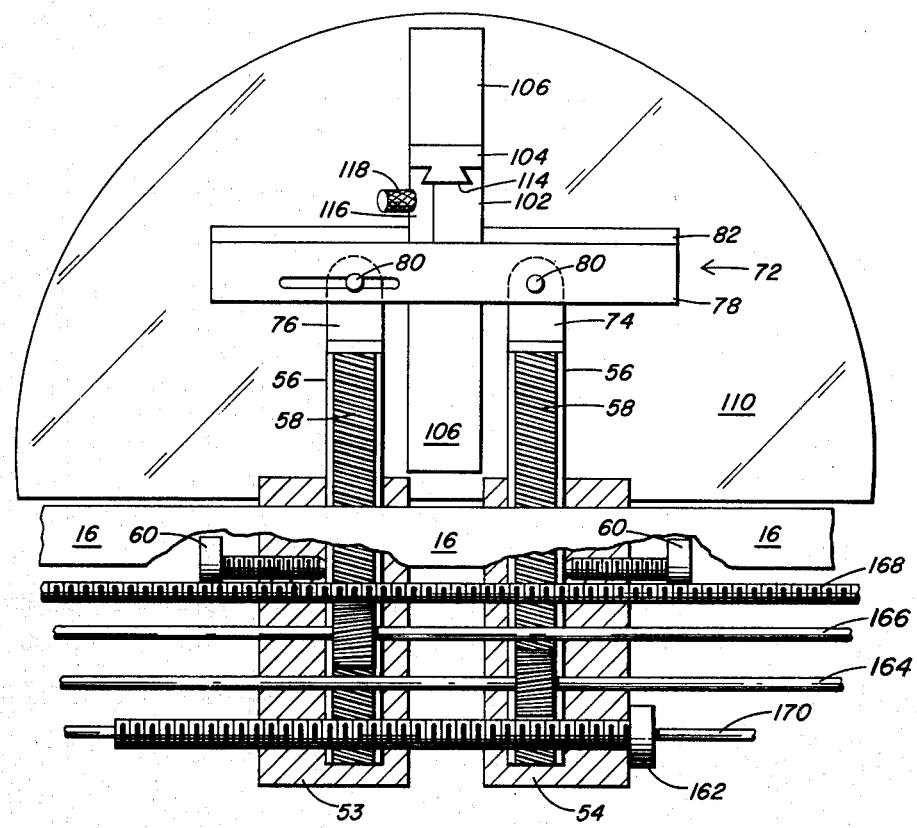
FIG. 2 is an enlarged view, along line 2—2 of FIG. 1, of the left bridge and adjustable brackets, the right bridge and brackets being substantially a mirror image thereof except for the absence of the protractor.

Along right frame segment 12 ride right front block 51 and right rear block 52. Along left frame segment 16 ride left rear block 53 and left front block 54. Each block is hollow and is penetrated front to back not only by the frame segment on which it rides, but by four horizontal rods, hereinafter described. Each block has in it a vertical slot just outward of the frame segment. In each slot rides an open-topped rectangular post 56 calibrated on its outer face and bearing on its inner face a rack 58 driven by a pinion inside the block, the pinion being mounted on one of the aforementioned rods. As shown in FIG. 2, a locking screw 60 projecting horizontally from the face of the block away from the adjacent block serves to lock the post 56 at the desired elevation. Anterior marker carriers 62 and posterior marker carriers 64 may be selectively inserted to slide part-way into the hollow posts during one phase of the use of the instrument. Offset shoulder 66 on the carriers 62, 64 limit downward movement inside the posts 56.

Figures 4, 5:
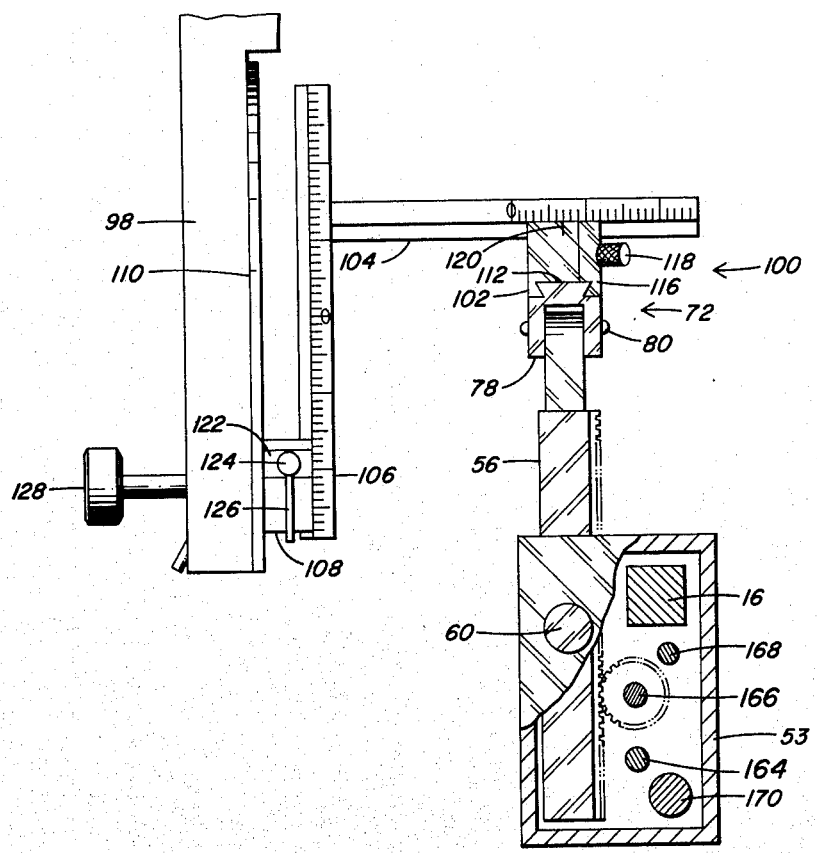
FIG. 4 is an enlarged rear detailed view of the left adjustable brackets, left bridge and one of the blocks on which the latter is mounted, partially broken away to show a cross-section thereof.
FIG. 5 is a left side view of the protractor and the lower end of the arc, mounted on a pin running through the protractor.

The actual anterior markers 68 and posterior markers 70 are small radio-opaque cylinders preferably embedded in clear Lexan plastic blocks comprising the carriers 62 and 64. Also adapted to fit onto the posts 56 in a subsequent phase of the use of the instrument are a pair of bridges 72, one of which spans right blocks 51 and 52, and the other of which spans left blocks 53 and 54, as shown in FIGS. 1, 2 and 4. Each bridge comprises three movable parts: a front upright 74, a rear upright 76 and an inverted trough section 78 over the uprights 74 and 76. The upright 74 and 76 are each configured like the marker carriers, and each is pierced by a horizontal radio-opaque pivot tube 80 which passes through the sidewalls of trough 78. The pivot of front upright 74 permits only rotational movement of trough 78 about upright 74, but longitudinal slots in the sidewalls of trough 78 permit the latter to slide forward and back in relation to rear upright 76, in addition to rotating. Thus, the rear blocks 52 and 53 may be moved relative to front blocks 51 and 54 while bridges 72 are in place. Integral with vertical parallel sidewalls of each trough 78 is a top 82 of anvil-like cross-section which is graduated and forms a runner for adjustable brackets to be described below.

The movement of the blocks 51-54 and the posts 56 within them is accomplished by adjustment of a plurality of knobs attached to a rod and gear system. The posts 56 adjust vertically, while the blocks adjust along a front-to-back or anterior-posterior (hereinafter referred to as AP) axis. On the left vertical face of each of the gearboxes 18 and 24 are provided a long-stemmed vertical adjustment knob and a short-stemmed AP adjustment knob.

As shown in FIG. 1, in the lower right corner of the face of left front gearbox 18 is front vertical adjustment knob 84, which moves the posts 56 of front blocks 51 and 54 simultaneously up or down and in the upper right corner of the face of left rear gearbox 24 is rear vertical adjustment knob 86 which moves the posts 56 of rear blocks 52 and 53 simultaneously up or down.

In the upper left corner of the face of front gearbox 18 is front AP adjustment knob 88 which simultaneously moves all four blocks equal distances forward toward segment 10 or back toward segment 14. In the lower left corner of the face of rear gearbox 24 is rear AP adjustment knob 90 which simultaneously moves rear blocks 52 and 53 equal distances forward or back in relation to front blocks 51 and 54.

As previously mentioned, the outer face of each post 56 is calibrated, allowing recording of the elevations to which the posts are adjusted by knobs 84 and 86. Similarly, the outer faces of right and left frame segments 12 and 16 are calibrated, allowing recording of AP positions of the blocks resulting from adjustment of knobs 88 and 90.

Figure 3:
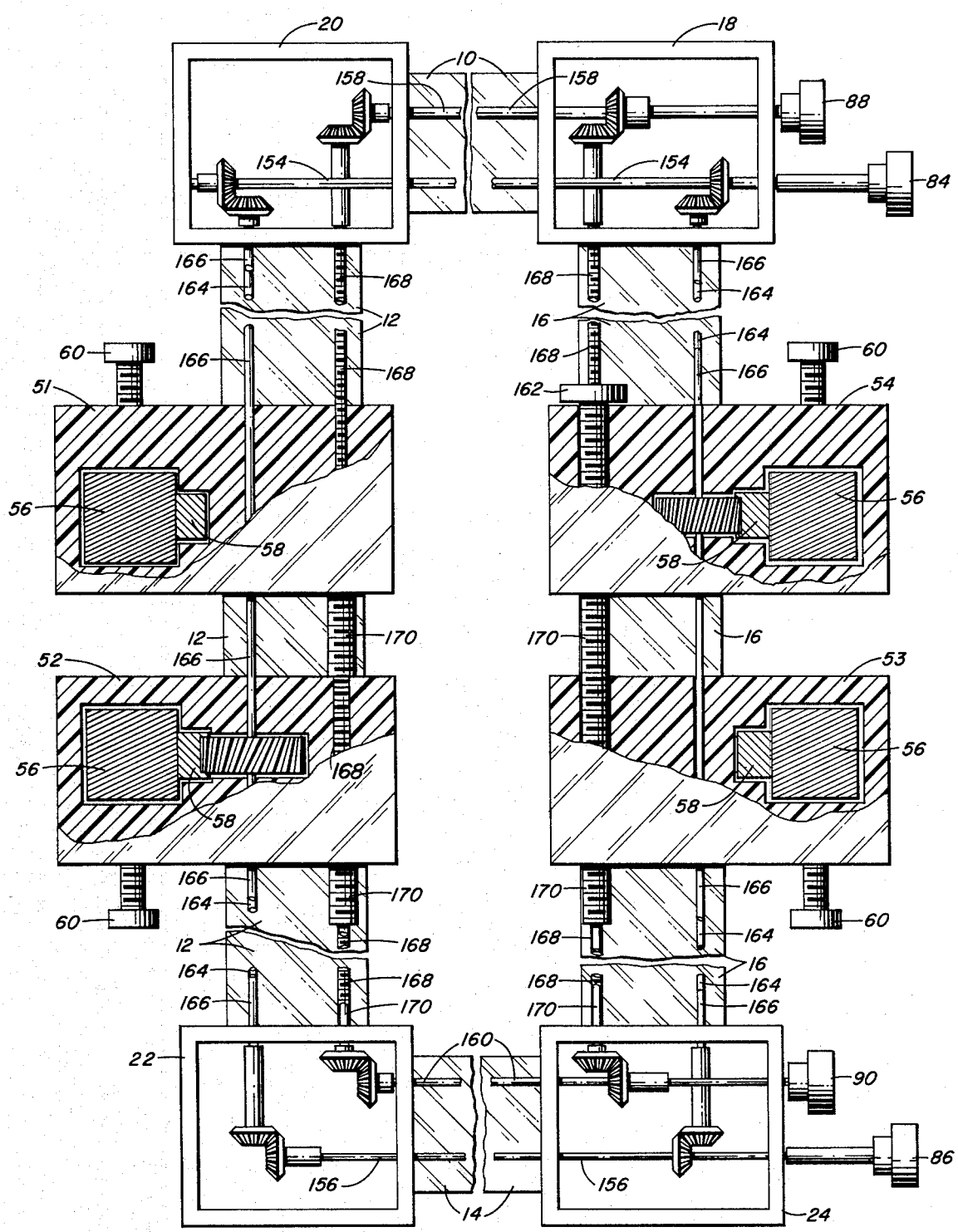
FIG. 3 is a fragmentary bottom view of the frame, showing the arrangement of gears in the gearboxes, the movable blocks, and the connecting rods therebetween, broken along two different planes.

FIG. 3 is a partially broken away view of the bottom of the stereotactic instrument, with frame segments 10, 12, 14 and 16 hatched for clarity. All references to components are in terms of their relation to the head; thus, "left" components appear on the right side of the FIG. and vice versa, and "lower" components in solid lines in the foreground, while "upper" components are shown in phantom or not at all in cases of superposition. Left and right blocks are broken away at separate levels.

Each of the four adjustment knobs 84, 86, 88 and 90 are mounted on a gearshaft which extends through the adjacent left gearbox laterally (left to right) into the corresponding right gearbox. Front vertical adjustment knob 84 is mounted on lower front gearshaft 154 which extends through left front gearbox 18 and is rotatably fixed in the outer wall of right front gearbox 20. Rear vertical adjustment knob 86 is mounted on upper rear gearshaft 156 which extends through left rear gearbox 24 and terminates in a bevel gear inside right rear gearbox 22. Front AP adjustment knob 88 is mounted on upper front gearshaft 158 which extends through left front gearbox 18 and terminates in a bevel gear just inside right front gearbox 20. Rear AP adjustment knob 90 is mounted on lower rear gearshaft 160 which extends through left rear gearbox 24 and terminates in a bevel gear just inside right rear gearbox 22.

Each of the four gearshafts bears two bevel gears, one in each of the gearboxes through which it passes, which mesh at right angles with other bevel gears mounted on one of the eight rods which penetrate the blocks and which are depicted in FIG. 3 running from the top of the FIG. to the bottom. The bevels of the eight rod gears all point outwardly, i.e., toward the front in the front gearboxes and toward the rear in the rear gearboxes. All rod gears are at the ends of their respective rods.

The eight rods are disposed in vertical pairs, with two vertical adjustment rods passing horizontally through the outer portion of the blocks, adjacent to the racks 58 on posts 56, and two AP adjustment rods passing horizontally through the inner portion of the blocks, below frame segments 12 and 16. Thus, there are two pairs of rods on the right, passing through blocks 51 and 52 and two other pairs on the left, passing through blocks 53 and 54.

Front vertical adjustment rods 164, shown in FIG. 3, and rear vertical adjustment rods 166, on which the former are superimposed in FIG. 3, have a longitudinal slot in them which serves as a rotational detent for the pinion which drives the rack 58 of the respective post 56. Each pinion approximates in length the interior dimension of its block, so that it will slide forward or back on its vertical adjustment rod as the surrounding block moves, but will not disengage from either its rack 58 or the slot in the rod on which it rides.

The pinions in front blocks 51 and 54 are mounted on front vertical adjustment rods 164 to drive the posts in blocks 51 and 54 up and down in response to turning of knob 84, while the pinions in rear blocks 52 and 53 are mounted on rear vertical adjustment rods 164 to drive the posts in blocks 52 and 53 up and down in response to turning of knob 86. The rods 164 and 166 are not threaded and do not influence the positions of the blocks 51, 52, 53 and 54 through which they slide.

As shown in FIG. 3, the two bevel gears on gearshaft 154 face in opposite directions, as do the two bevel gears on gearshaft 156. This is necessary to make the left and right vertical adjustment rods counter rotating with respect to each other. Since the pinions on the left side of the frame are to the right of their respective racks 58, while the pinions on the right side of the frame are to the left of their respective racks, the rods driving the pinions must be counter rotating to cause the racks 58 to be driven in the same direction at the same time in response to a given rotation of gearshaft 154 or 156.

The inner, AP adjustment rods, by contrast, are threaded so as to move the blocks. Front AP adjustment rods 168 are threaded over substantially their entire lengths and the apertures in the blocks 51 and 54 through which they pass are also threaded, so that turning knob 88 results in simultaneous and equal movement of all four blocks in the same forward or backward direction. Rear AP adjustment rods 170 fix the distance between front blocks 51 and 54 and rear blocks 52 and 53, causing the latter to move sympathetically with the former when rods 168 turn. When knob 88 and rods 168 are stationary, turning of rear AP adjustment knob 90 and, thus, rear AP adjustment rods 170 causes rear blocks 52 and 53 to simultaneously move toward or away from stationary front blocks 51 and 54. This is accomplished by fixing one end of a threaded portion of each rod 170 to a cap 162 on the front face of each front block and engaging that threaded portion with threads in the apertures in rear blocks 52 and 53.

Each of the rods is driven by a bevel gear at one end and rotatably snubbed just inside the gearbox at its other end. The front adjustment rods are snubbed inside the rear gearboxes and vice versa.

The centers of the upper surfaces of front and rear frame segments 10 and 14 each contain a plurality, preferably two, of spaced holes 92 for mounting, on prongs fitted into the holes, a midline marker carrier 94, which may be a rectangular block of Lexan or its equivalent. Attached to or embedded in each marker carrier is a vertical radio-opaque wire or strip which serves as the midline marker 96. When the frame is mounted on a patient's head, the third ventricle or cavity between the left and right hemispheres of the brain can be imaged on a fluoroscope and aligned with the front and rear midline markers 96 by extending some of the screws 38 and retracting others, thereby moving the frame relative to the patient's head.

After alignment of the midline, anterior and posterior markers, by a procedure hereinafter described, a semicircular arc 98 is rotatably mounted on bridges 72 by means of adjustable brackets 100, as shown in FIGS. 1 and 4.

As shown most clearly in FIGS. 2 and 4, adjustable brackets 100 comprise an AP carriage 102 riding on runner 82, a calibrated lateral runner 104 riding on carriage 102, a calibrated vertical runner 106 rigidly and orthogonally mounted on the outer end of lateral runner 104 and a vertical carriage 108. On one of the bracket sets 100, preferably the left, a protractor 110 is rigidly mounted on vertical carriage 108 to indicate the rotational position of arc 98.

The configurations of these elements are as follows: AP carriage 102 is basically cubical except for an inwardly splayed front-to-back groove 112 in its lower surface for receiving runner 82, a similarly splayed left-to-right groove on its upper surface and a detachable rectangular vertical locking member 116 held in a notch at the carriage's inside rear edge by a diagonal locking screw 118 penetrating the locking member 116 and threaded into a hole in carriage 102. The upper and lower ends of locking member 116 are beveled like the adjacent parts of carriage 102 so as to narrow the grooves 112 and 114 and lock runners 82 and 104 with a single adjustment when locking screw 118 is tightened. A single vertical stripe at the midpoint of the front and rear faces of carriage 102 is used for reading the calibration to which runner 104 is adjusted.

Lateral runner 104 has a rectangular upper face and a vertical cross-section like an upside-down anvil. The beveled lower portion rides in groove 114, while the rectangular upper portion has vertical front and rear faces with a laterally extending series of vertical stripe calibrations. The outer end away from the head is bonded to or integrally formed with vertical runner 106, whose horizontal cross-section is anvilshaped. The beveled portion of runner 106 faces away from runner 104. Runner 106 is calibrated with a vertically extending series of horizontal stripes. Each runner is long enough to allow its associated carriage to be adjusted through a sufficient range, preferably at least 55 mm in the AP direction, 45 mm in the vertical direction and 30 mm in the horizontal lateral direction either side.

Vertical carriage 108 is basically rectangular, with an inwardly splayed vertical groove along its inner face (adjacent the head) and a rectangular locking member 122 in a horizontal notch on its rear face intermediate its upper and lower ends. The locking member 122 is penetrated front to back by a horizontal locking screw 124 equipped with a projecting lever 126 to facilitate tightening of screw 124 in half a turn without colliding with the protractor 110. Carriage 108 has a threaded lateral hole (not shown) for receiving the mounting pin 128 of arc 98.

As shown in FIG. 5, each lower end of arc 98 includes a mounting block 130 through which pin 128 passes and from whose front face projects a locking screw 132 with attached lever 134 for gripping pin 128 and stopping rotation of arc 98 at a given angle, as read on protractor 110 with indicator 136 on top of mounting block 130.

As shown in FIG. 1, slidably mounted on arc 98 is rectangular electrode carrier 138. The arc, rectangular in cross-section, passes through a rectangular slot 140 in the electrode carrier, thereby preventing relative rotation and keeping the axis of carrier 138 radially aligned with the center of curvature of arc 98 wherever on the arc the carrier slides. A locking screw 141 locks the carrier 138 at any desired point on the arc 98.

Along the axis of carrier 138 but forward of rectangular slot 140 is a round longitudinal aperture 142 for receiving a calibrated electrode sheath 144. Around the sheath 144 and atop carrier 138 rides a collar 146 and locking screw 148 for regulating the extension of the sheath 144 to a calibrated value and controlling thereby the insertion depth of an electrode 150, which bears a circumferential stop too large to pass through the sheath 144.

METHOD OF USE

With the arc 98 detached, the stereotactic frame is placed around the patient's head. With the midline markers 96 mounted on the frame, the scalp is infiltrated with local anesthesia for receiving the sterile skull support points 36. An approximate alignment of the midline of the frame with the midline of the brain is made, using the nose and the shape of the head as visual references. The screws 38 are tightened until the points 36 support the frame on the head. A fluoroscope or image intensifier is then used to align the markers 96 with the middle of the third ventricle, which stands out because radio-opaque dye has been injected into it, and adjustments are made by extension or retraction of the appropriate screws 34. An X-ray film exposure is made for confirmation and counter nuts 40 are tightened.

The anterior and posterior markers are placed in posts 56 in the blocks on either side of the head. The fluoroscope is re-oriented to give a view of the third ventricle of the brain from the side, as if a vertical section were taken through the midline of the brain. Bundles of fibers at the front and back edges of the third ventricle, known respectively as the anterior commissure and the posterior commissure, are identified. The markers appear on the fluoroscope image as small circles.

With the patient immobilized, the front vertical and AP adjustment knobs are turned until the images of the anterior markers on the fluoroscope are superimposed on the anterior commissure. Similar adjustments are made with the rear vertical and AP knobs until the images of the posterior markers are superimposed on the posterior commissure. An X-ray film exposure is made in each case for confirmation, and the knobs 60 ae tightened for all posts 56. The relative positions of the blocks and their posts 56 are recorded.

Once the anterior and posterior commissure reference points have been established, the marker carriers 62 and 64 are removed from the posts 56 and replaced by the bridges 72. The bridges now represent lines precisely parallel to and equidistant from the reference line in the third ventricle between the anterior and posterior commissures. Since the location of various brain tissues in relation to this reference line is known from atlases of the brain, the relationship of these areas to the bridges is also known.

The adjustable brackets 100 are next slid into place on bridges 72, with all adjustments set to zero. The arc 98 is mounted on the brackets 100 by screwing pins 128 into carriages 108. The center of curvature of arc 98 is now on the reference line in the brain, and the tip of an electrode inserted to that center will always coincide with the center point from which all radii defining arc 98 emanate regardless of the position of rotation of arc 98 on pins 128, i.e. the tip of the electrode should touch the anterior commissure when introduced with its sheath set to the zero graduation. Before any electrode is inserted in the electrode carrier, though, the target tissue in the brain is located in relation to the reference line. Any lateral displacement is mimicked by movement of runners 104 in relation to carriers 102. Any anterior or posterior displacement is mimicked by movement of carriages 102 on runners 82 of bridges 72. Any vertical displacement is mimicked by movement of carriages 108 on runners 106. Equal adjustments are made on both sides of the head simultaneously.

The desired radial insertion path for the electrode is selected by rotation of the arc 98 into position and locking by means of screw 132, followed by sliding of electrode carrier 138 into position over the insertion point on the skull and locking with screw 141. Of course, the arc can be rotated out of the way temporarily for drilling of the insertion hole and replaced to the same position by referring to the reading on protractor 100.

The electrode is sheathed for most of its length, except 3-4 mm near the tip, and works by causing coagulation of tissue near the unsheathed tip when electricity is applied. The insertion depth for the electrode is selected by locking the collar 146 at the desired calibration on the electrode sheath 144 in the electrode carrier 138. Since the brain has no pain sensors inside it, general anesthesia is unnecessary and success of the coagulation treatment for Parkinson's disease or similar disorders can be judged by whether a patient's muscular tremors cease.

Sometimes, it is necessary to create bilateral lesions, that is, to coagulate tissue at corresponding positions in both the left and right hemispheres of the brain. This can be readily accomplished with the present apparatus by withdrawing the electrode after the lesion in one hemisphere has been created, loosening the locking screws 118 on both left and right sets of adjustable brackets 100, sliding the arc 98 and attached adjustable brackets 100 off the bridges 72, sliding what had been the left brackets onto the right bridge and the right brackets onto the left bridge and resetting the position of the arc 98 on the protractor 110 to the same number of degrees from the vertical as before but in the opposite direction. The insertion of the electrode through a 2nd radially aligned burrhole will now permit creation of the second lesion in the exactly corresponding position in the second hemisphere of the brain without further measurement, calculation or X-ray exposures.

While the foregoing describes a preferred embodiment of the invention, those skilled in the art will appreciate that numerous modifications may be made of this invention without departing from its spirit. Therefore, it is not intended to limit the scope of this invention to the single embodiment illustrated and described. Rather, it is intended that the scope of this invention be determined by the appended claims and their equivalents.

What is claimed is:

1. A stereotactic instrument comprising;
   a rigid body-surrounding frame having segments adapted for fixation to the left and right of the skull,
   four fixation pins for securing said frame on, and rendering it motionless with respect to, the body,
   a pair of individually adjustable radio-opaque markers, each having a wall or walls less than 1 millimeter thick, mounted on each of said left and right segments and adapted to be aligned with radiographically visible reference points within the skull, following fixation of the frame to the skull,
   a bridge simulating outside the head the length and direction of a line between the anterior and posterior commisures of the brain, movable with respect to said frame segments, connecting each of said pairs of markers,
   means for maintaining said bridges coplanar with and in spaced parallel relation to each other and to a line between said reference points within the skull,
   a semi-circular arc having two ends, each pivotally mounted on one of said bridges,
   an electrode carrier slidably mounted on said arc, and
   an electrode sheath supported by said electrode carrier.

2. A stereotactic instrument as set forth in claim 1, wherein said arc is mounted on said bridges by means of a pair of adjustable graduated brackets comprising sliding dovetail means with locking screws for setting three coordinates, in a coordinate frame based upon said line between the anterior commisure and the posterior commisure, of a target.

3. A stereotactic instrument as set forth in claim 1, further comprising radio-opaque markers mounted on front and back segments of said frame for aligning said frame with the midline of the skull during a single fluoroscopic exposure.

* * * * *